United States Patent [19]

Valdiserri et al.

[11] Patent Number: 4,546,180

[45] Date of Patent: *Oct. 8, 1985

[54] PROCESS FOR PREPARING PHOSPHITE-ISOCYANURATES OLIGOMERS

[75] Inventors: Leo L. Valdiserri; Richard P. Woodbury, both of Belpre, Ohio

[73] Assignee: Borg-Warner Chemicals, Inc., Parkersburg, W. Va.

Related U.S. Application Data

[63] Continuation of Ser. No. 298,968, Sep. 3, 1981, abandoned.

[21] Appl. No.: 486,476

[22] Filed: Apr. 19, 1983

[ * ] Notice: The portion of the term of this patent subsequent to Mar. 15, 2000 has been disclaimed.

[51] Int. Cl.[4] .................. C07D 403/12; C07D 403/14
[52] U.S. Cl. ..................................................... 544/214
[58] Field of Search ......................................... 544/214

[56] References Cited

U.S. PATENT DOCUMENTS 3,121,082  2/1964  Guttag ................................ 544/214
4,085,283  4/1978  Den Otter et al. ................. 544/214
4,096,114  6/1978  Minagawa et al. ......... 260/45.8 NZ
4,140,660  2/1979  Den Otter et al. ................. 521/902
4,287,339  9/1981  Valdiserri ........................... 544/214

FOREIGN PATENT DOCUMENTS 7535099  11/1975  Japan ................................. 544/214
5425951   2/1979  Japan ................................. 544/112
5430241   3/1979  Japan ................................. 544/214
1526603   9/1978  United Kingdom ............... 544/112

Primary Examiner—Henry R. Jiles
Assistant Examiner—J. G. Mullins
Attorney, Agent, or Firm—Richard J. Schlott

[57] ABSTRACT

A process for preparing certain phosphite-isocyanurate oligomers. The process requires the reaction of a trishydroxyalkyl isocyanurate with a tris-organophosphite and, optionally, an alcohol or alkylphenol. The process is promoted by an alkaline catalyst such as sodium methoxide. The oligomeric product is useful as a thermal stabilizer in polymer compositions.

8 Claims, No Drawings

PROCESS FOR PREPARING PHOSPHITE-ISOCYANURATES OLIGOMERS

CROSS REFERENCE TO RELATED APPLICATIONS

This application is a continuation of application Ser. No. 298,968, filed Sept. 3, 1981, now abandoned.

This invention relates as indicated to a process and, particularly, to a process according to which certain phosphite-isocyanurate oligomers are prepared. These phosphite-isocyanurate oligomers are effective to impart a high degree of thermal stabilization to a wide variety of polymers.

BACKGROUND OF THE INVENTION

Because of their outstanding properties, synthetic polymers are used in a wide variety of applications. They are used, for example, as fibers, films, coatings and shaped objects. In almost all of these applications, as well as in the processing of the polymers, a high degree of thermal stability is required. Many polymers are not themselves sufficiently stable at elevated temperatures or during use as to resist deterioration with the result that they develop color, lose strength, etc. These polymers can be fortified against such deterioration by the addition of small proportions of certain types of compounds.

Polymers which are susceptible to deterioration at elevated temperatures and which are benefited with respect to reduced deterioration by the presence of the phosphite-isocyanurates herein include olefin polymers, styrene polymers such as polystyrene, high-impact polystyrene, SBR, ABS resins and MBS resins, polyamides, polycarbonates, olefin polymers such as polypropylene, low density polyethylene, high density polyethylene, polyisoprene, EPDM polymers, and copolymers of ethylene, polyvinyl chloride, polyvinyl acetate, polyvinyl ethers, polyvinylacetals, polyesters, polyurethanes, and polyacrylonitrile.

Japanese Patent Publication No. 79/30241 deals with this problem. It shows polyethylene and polypropylene compositions containing 2,2',2''-(1,3,5-s-triazine-2,4,6-1H, 3H, 5H-trionyl) tris ethylene bis-(alkylphenyl) phosphites. A process for the preparation of such phosphites is not shown, but there is shown a process involving the reaction of triphenyl phosphite, hydrobisphenol A and 2,4-di-tert-butyl phenol. The product of that process is not identified.

SUMMARY OF THE INVENTION

The invention of the present application is a process for preparing phosphite-isocyanurate oligomers comprising preparing a mixture of 1.0 mol of a tris-hydroxyalkyl isocyanurate wherein the alkyl is ethyl or 2-methylethyl and from about 0.8 to about 4 mols of a phosphite having the structure (RO)$_3$P wherein R is aryl, cycloalkyl or alkyl, heating said mixture at a temperature of from about 50° to about 200° C. to form a clear mixture and then distilling away the phenol or alcohol formed during the heating step.

DESCRIPTION OF THE PREFERRED EMBODIMENTS

Preferred R groups in the above formula include as indicated, aryl, cycloalkyl and alkyl radicals. Illustrative species include aromatic hydrocarbon radicals such as phenyl, 1-napthyl, p-cresyl, o-cresyl, 4-tertiarybutylphenyl, phenylethylphenyl, nonylphenyl and 2,4-diisopropylphenyl; aliphatic hydrocarbon radicals such as methyl, ethyl, n-propyl, tertiarybutyl, n-butyl, n-octyl, isodecyl, n-dodecyl, tetradecyl, octadecyl and eicosyl; and cycloaliphatic hydrocarbon radicals such as cyclopentyl, cyclohexyl, 2-methylcyclohexyl, 2,4-dimethylcyclohexyl, 4-tertiarybutylcyclohexyl and 2-methylcyclopentyl. The R radicals may each contain 1-30 carbon atoms.

The phosphite-isocyanurate product of the above process is relatively stable at elevated temperatures, i.e., its melt viscosity remains fairly constant and its color virtually unchanged.

The above process proceeds most efficiently in the presence of a basic catalyst. The catalyst may be a basic metal compound such as a basic metal oxide, hydroxide, carbonate, bicarbonate or alkoxide. The metal may be alkali metal or alkaline earth metal. Alternatively, the catalyst may be an amine. Tertiary aliphatic hydrocarbon amines boiling above 100° C. are particularly contemplated. Preferred catalysts are the sodium alkoxides wherein the alkoxide contains 1-4 carbon atoms.

The relative proportions of phosphite to tris-hydroxyalkyl isocyanurate ordinarily are about 3:1, on a molar basis. More phosphite than this can be used, as indicated, but the use of a large stoichiometric excess of phosphite results in the formation of a product mixture containing very little if any oligomer.

In addition to the phosphite and tris-hydroxyalkyl isocyanurate reactants as above, the process mixture may also contain an alcohol or alkylphenol. Alcohols and alkylphenols containing 2-30 carbon atoms are contemplated. Specific illustrative embodiments include methanol, ethanol, n-propyl alcohol, n-butyl alcohol, 2-ethylhexanol, n-decanol, undecanol-1, n-dodecanol, isododecyl alcohol, n-octadecanol, eicosyl alcohol, n-butylphenol, nonylphenol, dodecylphenol, octadecylphenol, etc. The ratio of alcohol or alkylphenol to tris-hydroxyalkyl isocyanurate may range up to about 10, on a molar basis.

The temperature of the heating step may vary between about 50° C. and about 200° C. Preferably, the temperature is between about 80° C. and about 180° C. The process mixture becomes clear as the reaction proceeds and then the by-product phenol or alcohol as the case may be, is removed from the process mixture by distillation at reduced pressure, i.e., generally, by heating to a final temperature of, for example, 135°-180° C./0.1-0.2 mm.

The concentration of phosphite-isocyanurate in stabilized polymer compositions ranges from about 0.01 to about 1.0 pph (parts per hundred parts of olefin polymer).

The polymer compositions of the invention may also contain a phenolic antioxidant, which acts to enhance the effectiveness of the phosphite additive. Illustrative phenolic compounds include phenol esters, especially esters of 3-(3',5'-ditertiarybutylphenyl)propionic acid such as the stearyl, lauryl, ethylene, trimethylene, propylene, 1,6-hexylene, neopentyl, glyceryl and pentaerythritol esters, i.e., those having a molecular weight greater than about 425; substituted phenols and naphthols wherein the phenolic group is "hindered" by a bulky group, e.g. tertiary butyl, tertiary amyl, cyclohexyl and the like, in the ortho position, such as butylated hydroxytoluene (BHT), 2-tertiarybutyl-1-napthol, o-cyclohexylphenol, o-tertiarybutyl-phenol, etc.

The amount of phenolic antioxidant to be used in these compostions will range from about 0.01 to about 1.0 pph.

Other types of well-known polymer additives may also be used in the polyethylene compositions of this invention for their known purposes, including particularly metal carboxylates such as calcium stearate, magnesium stearate, zinc laurate and the like. Also, oxides of these methods, UV stabilizers and sulfur synergists.

Illustrative methods of preparation are as follows:

EXAMPLE I

A mixture of 13.06 g. (0.05 mol) of tris-hydroxyethyl isocyanurate, 46.54 g. (0.15 mol) of triphenyl phosphite, 23.74 g. (0.15 mol) of decyl alcohol and 0.10 g. (0.002 mol . . . 4 mol percent of the tris-hydroxyethyl isocyanurate) of sodium methoxide is heated with stirring at 100° C. for 30 minutes. The clear reaction mixture is stripped to a final distillation temperature of 135° C./1 mm. to yield 26.72 g. of phenol. The residue is 53.93 g. of a slightly cloudy, colorless oil which is shown by high performance liquid chromatography (HPLC) to contain 75-80% of the desired oligomer, 10% of diphenyldecyl phosphite, 10% of didecylphenyl phosphite and 3-5% of decyl alcohol.

EXAMPLE II

A mixture of 13.06 g. (0.05 mol) of tris-hydroxyethyl isocyanurate, 46.54 g. (0.15 mol) of triphenyl phosphite, 47.48 g. (0.30 mol) of decyl alcohol and 0.10 g. (0.002 mol) of sodium methoxide is heated with stirring at 100° C. for 30 minutes. The clear reaction mixture is stripped to a final distillation temperature of 135° C./1 mm. to yield 42.84 g. of phenol. The residue weights 61.64 g. It contains about 10% each of tridecyl phosphite and phenyldidecyl phosphite and traces of triphenyl phosphite and decyl alcohol, the rest being the desired oligomeric polyphosphite (as shown by HPLC).

EXAMPLE III

The procedure of Example II is followed using the following amounts of reactants:

13.06 g. (0.05 mol) of tris-hydroxyethel isocyanurate
46.54 g. (0.15 mol) of triphenyl phosphite
0.10 g. (0.002 mol) of sodium methoxide The amount of phenol recovers is 11.36 g. (0.12 mol). The oligomeric product is a cloudy, colorless, very viscous liquid shown by HPLC to contain 42% of triphenyl phosphite.

EXAMPLE IV

A mixture of 6.53 g. (0.025 mol) of tris-hydroxyethyl isocyanurate, 51.60 g. (0.075 mol) of tris-(nonylphenyl) phosphite, 20.29 g. (0.075 mol) of stearyl alcohol and 0.04 g. (0.00075 mol) of sodium methoxide is heated with stirring at 125° C. for 30 minutes. The resulting clear mixture then is stripped to a final temperature of 180° C./0.15 mm. to yield 27.49 g. of nonylphenol as distillate. The residual oligomeric product is a clear yellow liquid weighing 46.29 g. It contains only traces of nonylphenol and stearyl alcohol.

EXAMPLE V

The procedure of Example IV is followed using the following amounts of reactants:

6.53 g. (0.025 mol) of tris-hydroxyethyl isocyanurate
51.60 g. (0.075 mol) of tris-(nonylphenyl) phosphite
40.75 g. (0.150 mol) of stearyl alcohol
0.04 g. (0.00075 mol) of sodium methoxide The amount of nonylphenol recovered is 41.38 g. (0.20 mol). The oligomeric product, a white waxy solid weighing 50.79 g., contains only traces of nonyl phenol, stearyl alcohol and tris-(nonylphenyl) phosphite, as shown by HPLC.

The relative stability of polymer compositions containing the phosphite-isocyanurates of this invention is shown by data obtained as follows: A mixture of 100 parts of an ABS resin (containing 30% of polybutadiene), 1.5 parts of a lubricant, 5.1 parts of titanium dioxide pigment and 0.50 part of phosphite stabilizer is processed in a Banbury mixer, then on a 2-roll mill and the resulting sheet cut into strips which are then granulated. These are injection molded into sample specimens at 450° F. and 550° F. and the color of each such specimen noted. The difference in color (between samples molded at these two temperatures) is taken as an indication of the relative stability of the compositions of the specimens. The data is shown in Table I.

TABLE I

| Phosphite | (Color Difference) |
|---|---|
| Octyl diphenyl phosphite | 4.80 |
| Product of Example I | 1.87 |

Octyl diphenyl phosphite is a well-known polymer additive, used extensively to impart desired thermal stability to ABS resins. The data above shows the clear superiority of the phosphite-isocyanurate herein as an ABS resin stabilizer.

The efficacy of the phosphite-isocyanurates as polymer additives is shown further by test data (shown in Table II) acquired by the following test procedure: Granulated compositions as above are divided into two portions; one portion is compression molded into plaques and these plaques assigned a color rating; the other portion is extruded at 450° C. into a sheet which also is rated for color. A comparison of the two color ratings affords a measure of the stabilizing influence of the phosphite addition in the polymer sample.

TABLE II

| Phosphite | (Color Difference) |
|---|---|
| Octyl diphenyl phosphite | 5.74 |
| Product of Example I | 3.19 |

Again, the superiority as a thermal stabilizing agent of the phosphite-isocyanurates herein is clearly shown.

Further evidence of the thermal stabilizing properties of the phosphite-isocyanurates is seen in the results of a test carried out as follows: Poly(ethyleneterephthalate) (having an intrinsic viscosity of 0.59), plus phosphite-isocyanurate, is mixed at 280° C. in a Brabender mixing head. Samples are withdrawn immediately after flux and every ten minutes thereafter for 60 minutes; the color ratings of the samples reflect the various stages of deterioration and, thus, the relative effectiveness of the phosphitic-isocyanurate additives as thermal stabilizers. The color ratings are determined on the basis of a scale of 1-10, 1 being colorless and 10 being yellow-brown. The data is shown in Table III.

TABLE III

| Phosphite (phr) | Color Rating | | | | | | |
|---|---|---|---|---|---|---|---|
| | 0 | 10 | 20 | 30 | 40 | 50 | 60 |
| None | 1 | 2 | 3 | 5 | 7 | 9 | 10 |
| Product of Ex. 2 (0.2) | 1 | 1 | 1 | 2 | 2 | 3 | 6 |
| Product of Ex. 3 (0.2) | 1 | 1 | 1 | 1 | 2 | 2 | 3 |
| Product of Ex. 3 (0.05) | 1 | 1 | 2 | 3 | 4 | 6 | 8 |

The efficacy of these phosphite-isocyanurates as stabilizers in vinyl chloride polymers is shown by the data in Table IV. Rigid test samples are subjected to a Mill Stability test at 325° F., samples being removed at 5-minute intervals and rated for color. The color rating is based on a scale of 1-8 where 1 is colorless and 8 is dark brown. Each sample contains the following:

| Parts | |
|---|---|
| 100 | poly (vinyl chloride) |
| 13 | MBS (impact modifier) |
| 3 | epoxidized soya |
| 3.3 | lubes and processing aids |
| 0.3 | calcium stearate |
| 0.15 | zinc stearate |

In addition to the above, sample B contained 0.5 parts of the product of Example 1.

TABLE IV

| Sample | (Min) | | | | | | |
|---|---|---|---|---|---|---|---|
| | 0 | 5 | 10 | 15 | 20 | 25 | 30 |
| A | 1.5 | 6 | 6 | 6 | 7 | 8 | F* |
| B | 1.0 | 2.5 | 2.5 | 2.0 | 2.0 | 2.5 | 3.0 |

*F indicates catastrophic failure of the ample.

All parts and percentages herein, unless otherwise expressly stated, are by weight.

We claim:

1. A process for preparing phosphite-isocyanurate oligomers comprising preparing a mixture of 1.0 mol of tris-hydroxyalkyl isocyanurate wherein the alkyl is ethyl or 2-methylethyl, from about 0.8 to about 4 mols of a phosphite having the structure $$(RO)_3P$$

wherein R is phenyl, alkylphenyl, alkyl or cycloalkyl, the alkyl in each case having 1-9 carbon atoms, and from about 3.0 to about 6.0 mols of an alcohol or alkylphenol having 2-30 carbon atoms, said alcohol or alkylphenol having a higher boiling point then the alcohol or phenol ROH which is derivable from $(RO)_3P$, heating said mixture in the presence of a basic catalyst at from about 50° C. to about 200° C. to form a clear mixture and then distilling away the phenol or alcohol formed during the heating step.

2. The process of claim 1 wherein R is phenyl.
3. The process of claim 1 wherein R is alkylphenyl.
4. The process of claim 1 wherein R is alkyl.
5. The process of claim 1 wherein R is cycloalkyl.
6. The process of claim 1 wherein the alcohol contains 8-20 carbon atoms.
7. The process of claim 1 wherein the alcohol is decyl alcohol.
8. The process of claim 1 wherein the alcohol is stearyl alcohol.

* * * * *